United States Patent
Choudary et al.

(10) Patent No.: US 6,617,454 B1
(45) Date of Patent: Sep. 9, 2003

(54) PROCESS FOR THE PREPARATION OF AMINE OXIDES

(75) Inventors: Boyapati Manoranjan Choudary, Andhra Pradesh (IN); Chinta Reddy Venkat Reddy, Andhra Pradesh (IN); Billakanti Veda Prakash, Andhra Pradesh (IN); Balagam Bharathi, Andhra Pradesh (IN); Mannepalli Lakshmi Kantam, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 10/113,208

(22) Filed: Mar. 28, 2002

(51) Int. Cl.$^7$ .................. C07D 413/00; C07D 217/22; C07D 211/02; C07D 211/08; C07D 233/08
(52) U.S. Cl. .................. 544/170; 544/358; 546/141; 546/185; 546/192; 546/242; 548/347.1
(58) Field of Search .................. 546/185, 141, 546/192, 242; 544/170, 358; 548/347.1

(56) References Cited

U.S. PATENT DOCUMENTS

| | | | |
|---|---|---|---|
| 3,283,007 A | 11/1966 | Chadwick | 260/583 |
| 3,424,780 A | 1/1969 | Sayigh | 260/453 |
| 4,565,891 A | 1/1986 | Correa et al. | 564/298 |
| 4,889,954 A | 12/1989 | Laurenzo et al. | 564/298 |
| 5,130,488 A | 7/1992 | Smith et al. | 564/298 |
| 5,563,288 A | * 10/1996 | Bastro | 564/568 |
| 6,323,367 B1 | 11/2001 | Choudary et al. | 564/298 |

OTHER PUBLICATIONS

BM Choudary et al., *Chem commun.*, 2001, 1736–1737.
Shun–Ichi Murahashi et al., *J. Org. Chem.*, 1990, 55, 1736–1744.
Robert W. Murray et al., *J. Org. Chem.*, 1996, 61, 8099–8102.
Walter W. Zajac, Jr. et al., *J. Org. Chem.*, 1988, 53, 5856–5860.
Kazuya Yamaguchi et al., *Chemical Abstract*, 1999.
Elizabeth Gardner et al., *Advanced Materials*, 2001, 13(16):1263–1266.
B.M. Choudary et al., *Tetrahedron Letters*, 1998, 39(21):3555–3558.
Kiyotomi Kaneda et al., *Chemical Abstract*, 2000.
Gerhard Laus, *J Chem. Soc., Perkin Trans.*, 2001, 2:864–868.

* cited by examiner

Primary Examiner—Alan L. Rotman
Assistant Examiner—Raymond Covington
(74) Attorney, Agent, or Firm—Morgan & Finnegan, LLP

(57) ABSTRACT

The present invention provides a process for the preparation of amine oxide by reacting a tertiary or a secondary amine with hydrogen peroxide as an oxidant in the presence of a recyclable heterogeneous catalyst comprising a layered double hydroxide exchanged with an anion in the presence of an additive selected from the group consisting of benzonitrile, propionitrile, isobutyronitrile, benzamide and isobutyraride.

16 Claims, No Drawings

PROCESS FOR THE PREPARATION OF AMINE OXIDES

FIELD OF THE INVENTION

The present invention relates to an improved process for the preparation of high quality amine oxides from secondary and tertiary aliphatic amines by Mg—Al—O—t—Bu hydrotalcites using benzonitrile as an additive. More particularly, the present invention relates to an improved process for the preparation of amine oxides from secondary and tertiary aliphatic amines useful in the preparation of hair conditioners, shampoos, toothpaste, laundry detergent powder, fabric softeners, toilet soap bars, cosmetics and surfactants as well as in other applications as synthetic intermediates and excellent spin trapping reagents.

BACKGROUND OF THE INVENTION

Amine N-oxides hold a key position in the chemistry of heterocycles as well as in biomedical area. The tertiary amine oxides are widely used in treatment of fabrics and preparation of hair conditioners, shampoos, toothpaste, laundry detergent powder, fabric softeners, toilet soap bars and cosmetics as well as in other applications. They were also used as stoichiometric oxidants in metal catalysed dihydroxylation and epoxidation reactions of olefins. On the other hand, the oxides derived from secondary amines, called nitrones are highly valuable synthetic intermediates and excellent spin trapping reagents. In particular nitrones are excellent 1,3 dipoles and have been utilized for the synthesis of various nitrogen containing biologically active compounds e.g. alkaloids and lactams.

Conventionally tertiary amine oxides are prepared by oxidation of respective tertiary amines with strong oxidising agent like aqueous hydrogen peroxide in a solvent such as water, lower alcohol, acetone or acetic acid. A dilute or preferably concentrated (30–90% by weight) hydrogen peroxide solution is added in stoichiometric or greater amount to an aqueous solution containing the tertiary amine to obtain amine oxide, (U.S. Pat No. 3,215, 741). The drawback is that the reaction transforms into a gel resembling a thick paste long before completion of reaction, which retards further reaction. The yields are only 30–40% by weight of amine oxide. Later several methods such as incorporation of catalyst and/chelating agent have been developed to in order to increase the quality and yields of the product.

In case of secondary amines, the classical methods involve the condensation of N-monosubstituted hydroxylamines with carbonyl compounds or the direct oxidation of N,N-disubstituted hydroxylamines. Later direct oxidation of secondary amines using several oxidising systems such as $R_2C(\mu-O_2)$, $Na_2WO_4$—$H_2O_2$, $SeO_2$, TPAP-NMO and UHP-M (M=Mo, W), MTO—$H_2O_2$ have been developed to accomplish nitrones under homogenous conditions. The drawback in all the above cases is the difficulty in recovering the homogeneous catalyst/reagents from the reaction mixture.

Reference is made to a U.S. Pat. No. 3,283,007 wherein the oxidation of tertiary amines using diethelene trianine penta/tetra acetic acid as chelating agent and sometimes contaminated with heavy metals is recommended to improve the yield. The hydrogen peroxide solution employed has concentration of at least 30–75% by weight. The disadvantages of this process are high reaction temperatures ranging between 40–100° C., longer reaction periods, and lower yields of amine oxides.

Reference is made to U.S. Pat. No. 3,424,780, wherein high yields of tertiary amine oxides are achieved by carrying the oxidation of tertiary amine with 30–70% by weight of aqueous hydrogen peroxide using 0.01 to 2% weight of carbondioxide, in presence of a chelating agent, tetra acetylene diamine, a salt thereof, polyphosphates, stannates, a hydroxy carboxylic acid salts or the salt of poly carboxylic acid. The disadvantages of this process are longer reaction periods and the amine oxide formed is intensively coloured when carbon dioxide atmosphere is used to speed up the reaction and this method necessitates injecting a gas which requires handling facilities. Another disadvantage is more than 30% by weight of hydrogen peroxide is not environmentally friendly.

Reference is made to another U.S. Pat. No. 4,889,954 wherein the tertiary amines are reacted in high yields to give the corresponding amine oxides with a low content of nitrosamine, the oxidation of tertiary amine being carried out in the presence of a dialkyl carboxylic acid ester as catalyst and if appropriate, ascorbic acid as a co-catalyst using 45–70% by weight of hydrogen peroxide. The drawbacks in the above process are the requirement of frequent addition of water to avoid gel formation, high reaction temperatures, longer reaction periods and difficulty in separation of the catalyst from the reaction mixture.

Reference is made to another U.S. Pat. No. 4,565,891 wherein octacyano molybdate or iron salts are used as catalysts and molecular oxygen for oxidation of tertiary amines at high pressures and temperatures. The main drawback of this process is the need of very high temperature of 90–130° C. and low yields of amine oxide reporting 11–52% of conversion.

Reference is made to a U.S. Pat. No. 5,130,488 wherein the solid amine oxide can be prepared by reacting a tertiary amine with hydrogen peroxide using carbon dioxide in presence of acetate and cooling to precipitate the product. This process is superior to previously known methods of preparing amine oxides. However, its use can sometimes lead to cleavage of the solvents, plating on the walls of the vessel used for the precipitation, contamination of the product with residual peroxide, and or discoloration of the product.

Reference is made to a publication by Walter W. Zajac et al., J. Org. Chem.; 53, 5856, 1988 wherein the oxidation of secondary and tertiary amines using 2-sulfonyloxyaziridines (Davis Reagents) were reported. The drawback of the above process is, the reagent was used in stoichiometric amounts.

Reference is made to a publication by Shun-Ichi Murahashi et al., J. Org. Chem.; 55, 1736, 1990 wherein the sodium tungstate was used as catalyst for the oxidation of secondary amines. The drawback is difficulty in recovery of the catalyst from homogeneous conditions.

Reference is made to publication by Murraay et al., J. Org. Chem.; 61, 8099, 1996 wherein methyltrioxorhenium was used as a catalyst in oxidation of secondary amines. The drawback is the difficulty in recovery of the catalyst.

Reference is made to publication by Choudary et al., Chem. Commun.; 2001, 1736 wherein tungstate-exchanged Mg—Al—LDH was used as a catalyst in oxidation of tertiary amines. The time taken for the reaction is 3–4 h.

OBJECTS OF THE INVENTION

The main object of the present invention is to provide an eco-friendly and simple process for N-oxidation of secondary and tertiary amines using layered double hydroxides exchanged with anion of alkoxides as a catalyst which is cheaper, non-corrosive and recyclable catalyst utilising only lower percentage of hydrogen peroxide at moderate temperatures to give high yields of product.

Another object of the present invention is to provide an improved process for the preparation of tertiary amine oxides and secondary amine oxides (nitrones), widely used in detergents, shampoos, fabric softers and biomedical area.

Another object of the present invention is the use of non-corrosive and low cost heterogeneous catalysts i.e. layered double hydroxides exchanged with anion of tert-butoxide, isopropoxide, ethoxide and methoxide.

SUMMARY OF THE INVENTION

The present invention describes a recyclable heterogeneous catalyst, i.e. layered double hydroxides exchanged with anion of tert-butoxide, isopropoxide, ethoxide or methoxide that catalyses the oxidation of secondary and tertiary amines in presence of an additive selected from benzonitrile, propionitrile, acetonitrile, isobutyronirtile, benzamide, isobutyramide. The advantages such as low cost of the catalyst, reusability for several times and its ability to oxidise the amines at 10–65° C. in a shorter period make the present invention as a promising candidate for a clean and efficient industrial route to amine oxide preparation.

Accordingly the present invention provides a process for the preparation of amine oxide which comprises reacting a tertiary or a secondary amine with hydrogen peroxide as an oxidant in presence of a recyclable heterogeneous catalyst comprising a layered double hydroxide exchanged with an anion selected from the group containing tert-butoxide, ethoxide, isopropoxide and methoxide in the presence of an additive selected from the group consisting of benzonitrile, propionitrile, isobutyronitrile, benzamide and isobutyramide, in an organic solvent, and separating the product and recovering the additive.

In one embodiment of the invention, the reaction is carried out at a temperature in the range of 10–65° C. for a period of 0.5–5 hours under continuous stirring and the product is separated by filtration and subsequent evaporation of the solvent.

In a further embodiment of the invention, the layered double hydroxides exchanged with said anion is of the formula I: $[M^{II}_{(1-x)}M^{III}_x(OH)_2][M^{n-}]_{x/2}\cdot zH_2O$, derived from LDH having formula II $[M^{II}_{(1-x)}M^{III}_x(OH)_2][A^{n-}]_{x/2}\cdot zH_2O$, wherein $M^{n-}$ is an anion of tert-butoxide, isopropoxide, ethoxide and methoxide, An is an interstitial anion selected from nitrate, chloride and carbonate, $M^{II}$ is a divalent cation selected from $Mg^{2+}$, Mn2+, $Fe^{2+}$, $V^{2+}$, $Co^{2+}$, $Ni^{2+}$, $Cu^{2+}$, $Zn^{2+}Pd^{2+}$, and $Ca^{2+}$, and $M^{III}$ is a trivalent ion selected from group consisting of $Al^{3+}$, $Cr^{3+}$, $V^{3+}$, Mn 3+, Fe3+, $Co^{3+}$, $Ni^{3+}$, Rh3+, $Ru^{3+}$, $Ga^{3+}$ and $La^{3+}$.

In another embodiment of the invention, the tertiary amine is of the general formula $R^1R^2NR^3$ wherein $R^1$, $R^2$ and $R^3$ are the same or different and are straight-chain or branched chain groups selected from alkyl, alkenyl and aralkyls having $C_1$–$C_{24}$ carbons, and preferably are selected from imidazolines pyridines such as dimethyl decyl amine, dimethyl docyl amine and dimethylbenzylamine; N-substituted piperazines, and N-substituted morpholines such as N-substituted morpholine is N-methylmorpholine.

In another embodiment of the invention, the secondary amine is of the general formula $R^1R^2NH$ wherein $R^1$ and $R^2$ are the same or different and are straight-chain or branched chain groups selected from alkyl, alkenyl and aralkyls having Cl-$C_{24}$ carbons, and cyclic amines.

In another embodiment of the invention, the secondary amine is selected from dibutyl amine, dibenzyl amine, N-benzyl phenethylamine, N-phenyl benzylamine, piperidine and 1,2,3,4 tetrahydro isoquinoline.

In another embodiment of the invention, 30% by weight of aqueous hydrogen peroxide is added slowly in a controlled manner during the period specified.

In another embodiment of the invention, the catalyst is 6–14% by weight of alkoxides selected from tert-butoxide, ethoxide, isopropoxide and methoxide.

In another embodiment of the invention, the reaction is effected at a temperature in the range of 10 to 65° C. for 1–6 hours.

In another embodiment of the invention, the organic solvent is selected from methanol, ethanol, 1-propanol, 2-propanol, 1-butanol, 2-butanol and isobutyl alcohol.

In another embodiment of the invention, the amount of hydrogen peroxide used ranges between 2 to 6 moles per mole of secondary or tertiary amine.

In another embodiment of the invention, the amount of additive used is mole per mole of amine.

DETAILED DESCRIPTION OF THE INVENTION

The present invention provides an improved process for the preparation of amine oxides of a very high quality which comprises reacting tertiary and secondary amines with hydrogen peroxide as an oxidant in presence of a recyclable heterogeneous catalyst, layered double hydroxides exchanged with anion of alkoxides selected from tert-butoxide, ethoxide, isopropoxide, and methoxide as catalysts in the presence of an additive selected from benzonitrile, propionitrile, isobutyronirtile, benzamide, isobutyramide in an organic solvent at a temperature ranging between 10–65° C. for a period of 1–2 hours under continuous stirring and separating the product by simple filtration and subsequently evaporation of solvents by known methods and recovering the additive for reuse. The heterogeneous catalyst used is the layered double hydroxides exchanged with the anion selected from a group consisting of tert-butoxide, isopropoxide, ethoxide and methoxide having formula I: $[M^{II}_{(1-x)}M^{III}_x(OH)_2][M^{n-}]_{x/2}\cdot zH_2O$, which is derived from LDH having formula II $[M^{II}_{(1-x)}M^{III}_x(OH)_2]$ $[A^{n-}]_{x/2}\cdot zH_2O$ where $M^{n-}$ is an anion of tert-butoxide, isopropoxide, ethoxide and methoxide, $A^{n-}$ is interstitial anion, selected from nitrate, chloride, carbonate and $M^{II}$ is a divalent cation selected from the group consisting of $Mg^{2+}$, Mn2+, $Fe^{2+}$, $V^{2+}$, $Co^{2+}$, $Ni^{2+}$, $Cu^{2+}$, $Zn^{2+}$ $Pd^{2+}$, or $Ca^{2+}$ and $M^{III}$ is a trivalent ion selected from the group consisting of $Al^{3+}$, $Cr^{3+}$, $V^{3+}$, Mn3+, $Fe^{3+}$, $Co^{3+}$, $Ni^{3+}$, Rh 3+, $Ru^{3+}$, $Ga^{3+}$or $La^{3+}$. The tertiary amines used are the formula $R^1R^2NR^3$ wherein $R^1$, $R^2$ and $R^3$, which may be the same or different, and are the straight-chain or branched-chain groups selected from alkyl, alkenyl and aralkyls having $C_1$–$C_{24}$ carbons selected from N,N- dimethyl decyl amine, N,N-dimethyl dodecyl amine, N,N-dimethylbenzylamine, triethylamine, tributylamine and cyclic amines selected from imidazolines pyrididines, N-substituted piperazines, N-substituted piperadines or N-substituted morpholines, e.g., N-methylmorpholine. The secondary amines used are having general formula $R^1R^2NH$ wherein $R^1$ and $R^2$ may be the same or different and are the straight-chain or branched-chain groups selected from alkyl, alkenyl and aralkyls having $C_1$–$C_{24}$ carbons, selected from dibutyl amine, dibenzyl amine, N-benzyl phenethylamine, N-phenyl benzylamine and cyclic amines selected from piperidine, 1,2,3,4, tetrahydro isoquinoline. The present invention aqueous hydrogen peroxide is added slowly in a controlled manner for a period ranges between 0–15 min. The catalyst introduced in the system is 6–14% by weight of anion of alkoxides selected from tert-butoxide, isopropoxide, ethoxide and methoxide. The organic solvents are preferably methonol, ethanol, isopropanol, 1-propanol, 1-butanol, 2-butanol and tert-butyl alcohol, acetonitrile, tetrahydrofuran, dichloromethane, dichloroethane.

The reaction is effected at a temperature in the range of 10 to 65° C. for 0.5–5 hours. The amount of hydrogen peroxide used is 2 to 6 moles per mole of amine. The amount of additive benzonitrile, propionitrile, acetonitrile, isobutyronirtile, benzamide or isobutyramide used is mole per mole of amine which can be recovered quantitatively and reused to make the process more economical. The novelty of the invention lies in the use of solid base catalyst for the first time for the N-oxidation of secondary and tertiary amines. The anion of alkoxides, intercalated in the layered double hydroxides, effectively catalyses the oxidation of amines to amine oxides. The filtrate-containing product was removed by decantation and the solid catalyst is recycled for several times by the addition of fresh substrates and solvent without the addition of fresh catalyst. The consistent activity for several cycles under moderate reaction conditions in shorter reaction times makes the process economical and possible for commercial realisation.

Scientific explanation

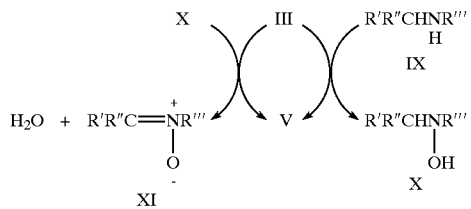

Scheme 1. The plausible reaction mechanism for the N-oxidation of amines catalysed by Mg—Al—O—t—Bu hydrotalcite using aqueous hydrogen peroxide.

The plausible reaction mechanism for the oxidation of tertiary and secondary amines is shown in Scheme 1. Initially hydrogen peroxide reacts with basic tert-butoxide of Mg—Al—O—t—Bu hydrotalcite (I) catalyst to form HOO⁻ species (11), which attacks the nirtile (IV) to generate a peroxycarboximidic acid (III) as an active intermediate oxidant. The active peroxycarboximidic acid further delivers electrophilic oxygen to nitrogen atom of tert-amine (VI) forming desired N-oxides (VII) and amide as by product (V). The secondary amine (IX) undergoes nucleophilic reaction with peroxycarboximidic acid (III) species to give hydroxylamine (X). Further oxidation of hydroxylamine (X) followed by dehydration gives nitrone (XI).

The following examples are given by way of illustration of the present invention and therefore should not be construed to limit the scope of the present invention.

EXAMPLE 1

Preparation of the Various Catalysts

1. Preparation of Mg—Al Hydrotalcite (LDH) Nitrate

Magnesium nitrate hexahydrate (30.8 g, 0.12 mol) and aluminium nitrate nonahydrate (15.0 g, 0.04 mol) were dissolved in 100 ml of deionised and decarbonated water. The pH of the solution was adjusted to 10 by adding 2 M NaOH. The resulting suspension was stirred for 2 h at room temperature. The precipitate hydrotalcite was collected by filtration under $N_2$ atmosphere and dried overnight at 80° C.

a) Preparation of Mg—Al—O—t—Bu Hydrotalcite (Catalyst A):

A solution of 0.1 M of potassium-tert-butoxide prepared by dissolution of 1.12 g of potassium-tert-butoxide in 100 ml of THF (freshly dried on metallic sodium) was taken in two-necked round bottomed flask. 1.214 g of Mg—Al hydrotalcite nitrate, as synthesised was added in one portion and the solution was stirred for 24 h, then filtered and washed several times with THF to yield 1.38 g of a white solid.

b) Preparation of Mg—Al—O—t—Bu Hydrotalcite (Catalyst B):

A solution of 0.1 M of potassium-tert-butoxide prepared by dissolution of 1.12 g of potassium-tert-butoxide in 100 ml of THF (freshly dried on metallic sodium) was taken in two-necked round bottomed flask. To this solution, 1.214 g of Mg-Al hydrotalcite nitrate-calcined (at 723 K for 6 h in a flow of air), was added in one portion and solution was stirred for 24 h, then filtered and washed several times with THF to yield 1.442 g of a white solid.

2. Preparation of Mg—Al Hydrotalcite (LDH) Chloride

Mg—Al—Cl hydrotalcite (3:1) is prepared as follows: A mixture of solution of $AlCl_3.9H_2O$ (12.07 g, 0.25 moles/liter) and $MgCl_2.6H_2O$ (30.49 g, 0.75 moles/liter) in deionised and decarbonated water (200 mL) and an aqueous solution of sodium hydroxide (16 g, 2 mol/liter) in deionised and decarbonated water (200 mL) were added simultaneously drop-wise from the respective burettes into the round bottomed flask. The pH of the reaction mixture was maintained constantly (10.00–10.2) by the continuous addition of 2 M NaOH solution. The suspension thus obtained was stirred for two hours under nitrogen atmosphere.

The solid product was isolated by filtration, washed thoroughly with deionised and decarbonated water, and dried at 70° C. for 15 h.

a) Preparation of Mg—Al—O—t—Bu Hydrotalcite (Catalyst C)

A solution of 0.1 M of potassium-tert-butoxide prepared by dissolution of 1.12 g of potassium-tert-butoxide in 100 ml of THF (freshly dried on metallic sodium) was taken in two-necked round bottomed flask. To this solution, 1.214 g of Mg—Al hydrotalcite chloride, was added in one portion and the solution was stirred for 24 h, then filtered and washed several times with THF to yield 1.382 g of a white solid.

b) Preparation of Mg—Al—O—t—Bu Hydrotalcite (Catalyst D)

A solution of 0.1 M of potassium-tert-butoxide prepared by dissolution of 1.12 g of potassium-tert-butoxide in 100 ml of THF (freshly dried on metallic sodium) was taken in two-necked round bottomed flask. To this solution, 1.214 g of Mg—Al hydrotalcite chloride-calcined (at 723 K for 6h in a flow of air), was added in one portion and solution was stirred for 24 h, then filtered and washed several times with THF to yield 1.478 g of a white solid.

3. Preparation of Mg—Al Hydrotalcite (LDH) Carbonate

Mg—Al—$CO_3$ hydrotalcite (3:1) is prepared as follows: An aqueous solution (0.280 L) containing $Mg(NO_3)_2.6H2O$ (0.2808 mol) and $Al(NO_3)_3.9H_2O$ (0.093 mol) (obtained from M/s. Fluka, a Sigma Aldrich Company, Switzerland) was added slowly to a second solution (0.280 L) containing NaOH (0.6562 mol) and $Na_2CO_3$ (0.3368 mol) in a one liter round bottomed flask under vigorous stirring. The addition took nearly 3 h. Then the slurry was heated to 338 K for 16 h. The precipitate formed was filtered off and washed with hot distilled water until the pH of the filtrate was 7. The precipitate was dried in an oven at 353 K for 15 h.

a) Preparation of Mg—Al—O—t—Bu Hydrotalcite (Catalyst E)

A solution of 0.1 M of potassium-tert-butoxide prepared by dissolution of 1.12 g of potassium-tert-butoxide in 100 ml of THF (freshly dried on metallic sodium) was taken in two-necked round bottomed flask. To this solution, 1.214 g of Mg—Al carbonate hydrotalcite calcined (at 723 K for 6 h in a flow of air), was added in one portion and solution was stirred for 24 h, then filtered and washed several times with THF to yield 1.428 g of a white solid.

EXAMPLE 2

Oxidation of N-methylmorpholine Catalysed by Mg—Al—O—t—Bu Hydrotalcite Using Aqueous Hydrogen Peroxide in Presence of Benzonitrile The two-necked flask was charged with 0.22 ml (2 mmol) of N-methylmorpholine, 10mg of catalyst B and benzonitrile (2 mmol) in 10 ml of methanol. To the mixture was added dropwise 0.66 ml (6 mmol) of a 30% by weight of aqueous solution of hydrogen peroxide for a period of 15 minutes. The temperature is raised to 65° C. and continues the reaction for another 15 minutes. After the completion of the reaction (followed by TLC), the catalyst was filtered off and washed with methanol. To the filtrate a small amount of manganese dioxide was added to decompose the unreacted hydrogen peroxide. The treated reaction mixture was filtered to remove the solid $MnO_2$ and concentrated under reduced pressure to obtain the product. The product thus obtained was purified by column chromatography to afford the corresponding amine oxide. N-methylmorpholine N-oxide of 98% yield was obtained. This product is commercially available from Fluka, Aldrich, Lancaster and Merck companies.

EXAMPLE 3

Oxidation of N-methylmorpholine Catalysed by Mg—Al—O—t—Bu Hydrotalcite Using Aqueous Hydrogen Peroxide in Presence of Benzonitrile: Recycle-I For recycle studies, a different protocol was adopted. After performing the reaction as stated above, the filtrate was siphoned out to obtain the product N-methylmorpholine N-oxide in 98% yield by column chromatography. Fresh amounts of N-methylmorpholine (2 mmol) and benzonitrile (2 mmol) were charged into the flask containing used catalyst. To the mixture was added drop-wise 0.66 ml (6 mmol) of a 30% by weight of aqueous solution of hydrogen peroxide for a period of 15 minutes. The temperature was raised to 65° C. and continued the reaction for another 15 minutes. The protocol was adopted to obtain the product as well as to perform another recycle and the results were tabulated in the Table 1.

EXAMPLES 4–7

The procedure was followed as in example 3 and the results are given in Table 1.

EXAMPLES 8–12

Oxidation of N-methylmorpholine using catalyst A, C, D, E and $KO^tBu$ was carried out following the procedure as in example 2 and the results are given in Table 1.

TABLE 1

The catalytic N-oxidation of N-methylmorpholine to N-methylmorpholine N-oxide in water using various solid base catalysts and their homogeneous analogues[a]

| Ex.No | Catalyst | Time(h) | Yield[c] |
|---|---|---|---|
| 2 | Mg—Al—O-t-Bu HT (Catalyst B) | 0.5 | 98 |
| 3 | Recycle 1 | 0.5 | 96 |
| 4 | Recycle 2 | 0.5 | 95 |
| 5 | Recycle 3 | 0.5 | 94 |
| 6 | Recycle 4 | 0.5 | 94 |
| 7 | Recycle 5 | 0.5 | 92 |
| 8 | Mg—Al—O-t-Bu HT (Catalyst A) | 0.5 | 96 |
| 9 | Mg—Al—O-t-Bu HT (Catalyst C) | 0.5 | 97 |
| 10 | Mg—Al—O-t-Bu HT (Catalyst D) | 0.5 | 97 |
| 11 | Mg—Al—O-t-Bu HT (Catalyst E) | 0.5 | 97 |
| 12 | $KO^tBu$ | 1.10 | 75 |

[a]Reaction conditions as exemplified in example 2
[b]Isolated yields

EXAMPLES 13–20

Oxidation of various tertiary amines using catalyst B was carried out following the procedure as in example 2 and the results are given in Table 2.

TABLE 2

Oxidation of tertiary amines catalysed by Mg—Al—O-t-Bu hydrotalcite in aqueous hydrogen peroxide using benzonitrile[a]

| Ex.No | Tertiary amine | Catalyst | Amine oxide | Time(min) | Yield[b] |
|---|---|---|---|---|---|
| 13 | Triethyl amine | B | Triethyl amine N-oxide | 30 | 98 |
| 14 | Tributyl amine | B | Tributyl amine N-oxide | 30 | 95 |
| 15 | N,N-dibutyl benzyl amine | B | N,N-dibutyl benzyl amine N-oxide | 45 | 96 |
| 16 | N-benzyl piperidine | B | N-benzyl piperidine N-oxide | 45 | 98 |
| 17 | N,N-dimethyl decyl amine | B | N,N-dimethyl decyl amine N-oxide | 30 | 98 |

TABLE 2-continued

Oxidation of tertiary amines catalysed by Mg—Al—O-t-Bu hydrotalcite in aqueous hydrogen peroxide using benzonitrile[a]

| Ex.No | Tertiary amine | Catalyst | Amine oxide | Time(min) | Yield[b] |
|---|---|---|---|---|---|
| 18 | N,N-dimethyl octyl amine | B | N,N-dimethyl octyl amine N-oxide | 30 | 98 |
| 19 | N,N-dimethyl benzyl amine | B | N,N-dimethyl benzyl amine N-oxide | 45 | 95 |
| 20 | N,N-dimethyl cyclohexylamine | B | N,N-dimethyl cyclohexyl amine N-oxide | 30 | 97 |

[a]Reaction conditions as exemplified in example 2
[b]Isolated yields

EXAMPLES 21–25

Oxidation of dibutyl amine using catalyst A, B, C, D, E was carried out following the procedures as in example 2 and the results are given in Table 3.

EXAMPLES 26–31

Oxidation of various secondary amines using catalyst B following the procedure as in example 2 and the results are given in Table 3.

TABLE 3

Oxidation of secondary amines catalysed by Mg—Al—O-t-Bu hydrotalcite in aqueous hydrogen peroxide using benzonitrile[a]

| Ex.No | Secondary amine | Catalyst | Amine oxide (nitrone) | Time(h) | Yield[b] |
|---|---|---|---|---|---|
| 21 | Dibutyl amine | A | N-butylidene-butylamine N-oxide | 5 | 96 |
| 22 | Dibutyl amine | B | N-butylidene-butylamine N-oxide | 5 | 98 |
| 23 | Dibutyl amine | C | N-butylidene-butylamine N-oxide | 5 | 96 |
| 24 | Dibutyl amine | D | N-butylidene-butylamine N-oxide | 5 | 96 |
| 25 | Dibutyl amine | E | N-butylidene-butylamine N-oxide | 5 | 97 |
| 26 | Dibenzyl amine | B | N-benzylidene benzylamine N-oxide | 5 | 75 |
| 27 | 2-methyl pyperidine | B | 6-Methyl, 2,3,4,5 tetrahydro pyridine N-oxide | 5 | 90 |
| 28 | Piperidine | B | 2,3,4,5 Tetrahydro pyridine N-oxide | 5 | 92 |
| 29 | Pyrrolidine | B | 1-pyrroline N-oxide | 3 | 72 |
| 30 | 1,2,3,4 Tetrahydro isoquinoline | B | 3,4, Dihydroisoquinoline N-oxide | 5 | 85 |
| 31 | Diisopropyl amine | B | N-(1-ethylethylidene)1-methylethyl amine N-oxide | 5 | 95 |

[a]Reaction conditions as exemplified in example 2
[b]Isolated yields

EXAMPLE 32

Regeneration of Benzonitrile From Benzamide

A two-necked flask was charged with of benzamide (0.0054 mol) and phosphorous pentoxide (1.2 g) in 10 ml of methanol. The mixture was stirred for 1 h at room temperature. After the completion of the reaction (followed by TLC), the mixture was concentrated on a rotovapor and benzonitrile was obtained quantitatively by vacuum distillation.

The Main Advantages of the Present Invention are

1. The present process is eco-friendly and very simple.
2. The catalyst is cheap, non-corrosive, recyclable for several times and heterogeneous in nature.
3. The reaction conditions are moderate, the reaction temperature ranges between 10–65° C.
4. The hydrogen peroxide used is 30% by weight, which is more environmentally friendly.
5. The process is economical.
6. The process is accomplished in a short time to afford high productivity.
7. The amount of effluents formed in this process is minimized because the catalyst and solvent are recovered/recycled and reused.
8. The process provides high quality of the product without resulting in gel formation, during the course of reaction.

We claim:

1. A process for the preparation of amine oxide which comprises reacting a tertiary or a secondary amine with hydrogen peroxide as an oxidant in presence of a recyclable heterogeneous catalyst comprising a layered double hydroxide exchanged with an anion selected from the group containing tert-butoxide, ethoxide, isopropoxide and methoxide in the presence of an additive selected from the group consisting of benzonitrile, propionitrile, isobutyronitrile, benzamide and isobutyramide, in an organic solvent, and separating the product and recovering the additive.

2. A process as claimed in claim 1 wherein the reaction is carried out at a temperature in the range of 10–65° C. under continuous stirring.

3. A process as claimed in claim 1 wherein the product is separated by filtration and subsequent evaporation of the solvent.

4. A process as claimed in claim 1 wherein the layered double hydroxides exchanged with said anion is of the formula I: $[M^{II}_{(1-x)}M^{III}_{x}(OH)_2][M^{n-}]_{x/2} \cdot zH_2O$, derived from LDH having formula II $[M^{II}_{(1-x)}M^{III}_{x}(OH)_2][A^{n-}]_{x/2} \cdot zH_2O$, wherein $M^{n-}$ is an anion of tert-butoxide, isopropoxide, ethoxide and methoxide, $A^{n-}$ is an interstitial anion selected from nitrate, chloride and carbonate, $M^{II}$ is a divalent cation selected from the group consisting of $Mg^{2+}$, $Mn2+$, $Fe^{2+}$, $V^{2+}$, $Co^{2+}$, $Ni^{2+}$, $Cu^{2+}$, $Zn^{2+}$ $Pd^{2+}$, and $Ca^{2+}$, and $M^{III}$ is a trivalent ion selected from the group consisting of $Al^{3+}$, $Cr^{3+}$, $V^{3+}$, $Mn^{3+}$, $Fe^{3+}$, $Co^{3+}$, $Ni^{3+,}$ $Rh^{3+}$, $Ru^{3+}$, $Ga^{3+}$ and $La^{3+}$.

5. A process as claimed in claim 1 wherein the tertiary amine is of the general formula $R^1R^2NR^3$ wherein $R^1$, $R^2$ and $R^3$ are the same or different and are straight-chain or branched-chain groups selected from alkyl, alkenyl and aralkyls having $C_1$–$C_{24}$ carbons.

6. A process as claimed in claim 1 wherein the tertiary amines are selected from the group consisting of imidazolines pyrididines, N-substituted piperazines, and N-substituted morpholines.

7. A process as claimed in claim 6 wherein the imidazolines pyrididine is selected from the group consisting of dimethyl decyl amine, dimethyl docyl amine and dimethylbenzylamine.

8. A process as claimed in claim 6 wherein the N-substituted morpholine is N-methylmorpholine.

9. A process as claimed in claim 1 wherein the secondary amine is of the general formula $R^1R^2NH$ wherein $R^1$ and $R^2$ are the same or different and are straight-chain or branched chain groups selected from the group consisting of alkyl, alkenyl and aralkyls having $C_1$–$C_{24}$ carbons, and cyclic amines.

10. A process as claimed in claim 1 wherein the secondary amine is selected from the group consisting of dibutyl amine, dibenzyl amine, N-benzyl phenethylamine, N-phenyl benzylamine, piperidine and 1,2,3,4 tetrahydro isoquinoline.

11. A process as claimed in claim 1 wherein 30% by weight of aqueous hydrogen peroxide is added slowly in a controlled manner during the period specified.

12. A process as claimed in claim 1 wherein the catalyst introduced in the system is 6–14% by weight of alkoxides selected from tert-butoxide, ethoxide, isopropoxide and methoxide.

13. A process as claimed in claim 1 wherein the reaction is effected at a temperature in the range of 10 to 65° C.

14. A process as claimed in claim 1 wherein the organic solvent is selected from the group consisting of methanol, ethanol, 1-propanol, 2-propanol, 1-butanol, 2-butanol and isobutyl alcohol.

15. A process as claimed in claim 1 wherein the amount of hydrogen peroxide used ranges between 2 to 6 moles per mole of secondary or tertiary amine.

16. A process as claimed in claim 1 wherein the amount of additive benzonitrile, propionitrile, acetonitrile, isobutyronirtile, benzamide, isobutyramide used is mole per mole of amine.

* * * * *